United States Patent
Norris et al.

(10) Patent No.: US 7,087,613 B2
(45) Date of Patent: *Aug. 8, 2006

(54) TREATING ABNORMAL CELL GROWTH WITH A STABLE POLYMORPH OF N-(3-ETHYNYLPHENYL)-6,7-BIS(2-METHOXYETHOXY)-4-QUINAZOLINAMINE HYDROCHLORIDE

(75) Inventors: Timothy Norris, Gales Ferry, CT (US); Jeffrey W. Raggon, North Stonington, CT (US); Richard D. Connell, East Lyme, CT (US); James D. Moyer, East Lyme, CT (US); Michael J. Morin, Waterford, CT (US); Shama M. Kajiji, Mystic, CT (US); Barbara A. Foster, Mystic, CT (US); Karen J. Ferrante, East Greenwich, RI (US); Sandra L. Silberman, Randolph, NJ (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/992,266

(22) Filed: Nov. 18, 2004

(65) Prior Publication Data

US 2005/0090500 A1  Apr. 28, 2005

Related U.S. Application Data

(63) Continuation of application No. 09/711,272, filed on Nov. 9, 2000, now Pat. No. 6,900,221.

(60) Provisional application No. 60/206,420, filed on May 23, 2000, provisional application No. 60/193,191, filed on Mar. 30, 2000, provisional application No. 60/164,907, filed on Nov. 11, 1999.

(51) Int. Cl.
*A61P 35/00* (2006.01)
*C07D 239/84* (2006.01)
(52) U.S. Cl. .................................................. 514/266.4
(58) Field of Classification Search ............. 514/266.4; 544/326
See application file for complete search history.

(56) References Cited

U.S. PATENT DOCUMENTS

| 3,800,039 | A | 3/1974 | Marquis et al. |
| 4,139,561 | A | 2/1979 | Onopchenko et al. |
| 4,216,341 | A | 8/1980 | Onopchenko et al. |

(Continued)

FOREIGN PATENT DOCUMENTS

AU  1842292  6/1992

(Continued)

OTHER PUBLICATIONS

Agharker, S., et al., "Enhancement of Solubility of Drug Salts by Hydrophilic Counterions: Properties of Organic Salts of an Antimalarial Drug," *Journal of Pharmaceutical Sciences* 1976, vol. 65, No. 5, pp. 747-749.

(Continued)

*Primary Examiner*—Thomas C. McKenzie
(74) *Attorney, Agent, or Firm*—Shu M. Lee; Kim T. Nguyen

(57) ABSTRACT

A method of monotherapy for a subject suffering from abnormal cell growth expressing the epidermal growth factor receptor (EGFR) which comprises orally administering to the subject a therapeutically effective amount of a crystalline polymorph of the hydrochloride salt of N-(3-ethynylphenyl)-6,7-bis(2-methoxyethoxy)-4-quinazolinamine so as to treat the subject.

14 Claims, 4 Drawing Sheets

U.S. PATENT DOCUMENTS

| | | | |
|---|---|---|---|
| 4,219,679 | A | 8/1980 | Onopchenko et al. |
| 4,255,313 | A | 3/1981 | Antonoplos et al. |
| 4,281,127 | A | 7/1981 | LeMahieu et al. |
| 4,305,751 | A | 12/1981 | Sabourin et al. |
| 4,322,420 | A | 3/1982 | Kobayashi et al. |
| 4,943,533 | A | 7/1990 | Mendelsohn et al. |
| 5,089,499 | A | 2/1992 | Barker et al. |
| 5,214,144 | A | 5/1993 | Tai et al. |
| 5,256,781 | A | 10/1993 | Primeau et al. |
| 5,457,105 | A | 10/1995 | Barker |
| 5,475,001 | A | 12/1995 | Barker |
| 5,580,870 | A | 12/1996 | Barker |
| 5,616,582 | A | 4/1997 | Barker |
| 5,639,881 | A | 6/1997 | Skibo et al. |
| 5,654,307 | A | 8/1997 | Bridges et al. |
| 5,686,458 | A | 11/1997 | Lee et al. |
| 5,707,992 | A | 1/1998 | Webber et al. |
| 5,710,145 | A | 1/1998 | Engel et al. |
| 5,747,498 | A | 5/1998 | Schnur et al. |
| 5,770,195 | A | 6/1998 | Hudziak et al. |
| 5,817,674 | A | 10/1998 | Clemence et al. |
| 5,821,246 | A | 10/1998 | Brown et al. |
| 5,948,784 | A | 9/1999 | Fujiwara et al. |
| 6,004,967 | A | 12/1999 | MacMahon et al. |
| 6,004,979 | A | 12/1999 | Clemence et al. |
| 6,130,218 | A | 10/2000 | Morsdorf et al. |
| 6,169,091 | B1 | 1/2001 | Cockerill et al. |
| 6,476,040 | B1 | 11/2002 | Norris et al. |
| 6,706,721 | B1 | 3/2004 | Allen et al. |
| 2002/0061304 | A1 | 5/2002 | Miller et al. |
| 2004/0102463 | A1 | 5/2004 | Allen et al. |

FOREIGN PATENT DOCUMENTS

| | | |
|---|---|---|
| AU | 3101093 | 1/1993 |
| AU | 3813095 | 11/1995 |
| CA | 2086968 | 11/1992 |
| CZ | 20003974 | 5/2001 |
| DE | 2936705 | 9/1979 |
| EP | 0498723 | 2/1992 |
| EP | 0520722 | 12/1992 |
| EP | 0566226 | 1/1993 |
| EP | 0579496 | 1/1994 |
| EP | 0602851 | 6/1994 |
| EP | 0635498 | 1/1995 |
| EP | 0635507 | 1/1995 |
| EP | 0667165 | 8/1995 |
| EP | 0787722 | 8/1997 |
| EP | 0837063 | 4/1998 |
| EP | 1044969 | 10/2000 |
| JP | 6205969 | 7/1985 |
| JP | 1048048 | 8/1987 |
| JP | 5208911 | 6/1992 |
| JP | 7309873 | 11/1992 |
| JP | 6192235 | 7/1993 |
| JP | 8099962 | 7/1993 |
| JP | 7101941 | 9/1993 |
| JP | 6336481 | 12/1993 |
| JP | 7118266 | 1/1994 |
| JP | 0673025 | 3/1994 |
| JP | 7126255 | 9/1994 |
| JP | 8151377 | 11/1994 |
| JP | 7188244 | 7/1995 |
| JP | 9165385 | 8/1995 |
| JP | 9221478 | 2/1997 |
| JP | 10036325 | 2/1998 |
| JP | 10036326 | 2/1998 |
| NZ | 0245662 | 1/1993 |
| RU | 2127263 | 1/1993 |
| WO | WO 9220642 | 11/1992 |
| WO | WO 9503283 | 2/1995 |
| WO | WO 9515758 | 6/1995 |
| WO | WO 9609294 | 3/1996 |
| WO | WO 9615118 | 5/1996 |
| WO | WO 9625422 | 8/1996 |
| WO | WO 9628430 | 9/1996 |
| WO | WO 9630347 | 10/1996 |
| WO | WO 9640210 | 12/1996 |
| WO | WO 9703069 | 1/1997 |
| WO | WO 9730035 | 8/1997 |
| WO | WO 9732856 | 9/1997 |
| WO | WO 9738983 | 10/1997 |
| WO | WO 9741896 | 11/1997 |
| WO | WO 9813354 | 4/1998 |
| WO | WO 9903803 | 1/1999 |
| WO | WO 9955683 | 11/1999 |
| WO | WO 9960023 | 11/1999 |
| WO | WO 0031048 | 2/2000 |
| WO | WO 0134574 | 5/2001 |
| WO | WO 0170255 | 9/2001 |

OTHER PUBLICATIONS

Berge, S., et al., "Pharmaceutical Salts," *Journal of Pharmaceutical Sciences* 1977, vol. 66 No. 1, pp. 1-19.

Bleicher, L., et al., "Aryl- and Hetero-Alkyne Coupling Reactions Catalyzed by Palladium on Carbon and CuI in an Aqueous Medium," *Synlett* Nov. 1995, pp. 1115-1116.

Bleicher, L., et al., "A Practical and Efficient Synthesis of the Selective Neuronal Acetylcholine-Gated Ion Agonist (S)-(-)-5-Ethynyl-3-(1-methyl-2-pyrrolidinyl)pyridine Maleate (SIB-1508Y)," *Journal of Organic Chemistry* 1998, vol. 63, No. 4, pp. 1109-1118.

Botros, S., et al., "Synthesis of Certain Nitro-quinazoline Derivatives Structurally Related to Some Chemotherapeutic Agents," *Egypt. J. Pharm. Sci.* 1972, vol. 13, No. 1, pp. 11-21.

Cerny, A., "Solvolysis of Some 1-(8a-ergolyinyl)-3,3-Diethylureas and Their Salts," *Collection-Czechoslovak Chem. Commun.* 1987, vol. 52, pp. 1331-1339.

Draetta, G. et al., Ann. Rep. Med. Chem. (1996) Academic Press, San Diego, pp. 241-246.

Driscoll D. et al., "Effect of Epidermal Growth Factor Receptor Tyrosine Kinase Inhibitor PD183805 on Vascular Endothelial Growth Factor Secretion from Several Tumor Models" (1999) XP-001014746 (Abstract only).

Hussain, M., et al., "Parenteral Formulation of the Kappa Agonist Analgesic, DuP 747, via Micellar Solubilization," *Pharmaceutical Research* 1992, vol. 9, No. 6, pp. 750-752.

Ishiwata T. et al., "Characterization of Keratinocyte Growth Factor and Receptor Expression in Human Pancreatic Cancer" (1998) *American Journal of Pathology* 153(1): 213-222.

Liu N. et al., "Comparative Phenotypic Studies of Duct Epithelial Cell Lines Derived from Normal Human Pancreas and Pancreatic Carcinoma" (1998) *American Journal of Pathology* 153(1) 263-269.

Melissaris, A.P. et al., "A Simple and Economical Synthetic Route to p-Ethynylaniline and Ethynyl-Terminated Substrates" (1994) J. Org. Chem. 59: 5818-5821.

Montalbetti, C. et al., "A Convergent Synthesis of Functionalized B-*seco* Taxane Skeletons" (1995) *Tetrahedron Letters* 36(33): 5891-5894.

Moyer, J., et al., "Induction of Apoptosis and Cell Cycle Arrest by CP-358,774, an Inhibitor of Epidermal Growth Factor Receptor Tyrosine Kinase," *Cancer Research* 1997, vol. 57, pp. 4838-4848.

Norris, T., et al., "Discovery of a New Stable Polymorph of 4-(3-ethynylphenylamino)-6,7-bis(2-methoxy-ethoxy)quinazolinium Methanesulfonate Using Near-Infrared Spectroscopy to Monitor Form Change Kinetics," *J. Chem. Soc., Perkin Trans.* 2000, vol. 2, pp. 1233-1236.

Norris, T., et al., "Discovery of a New Stable Polymorph of 4-(3-ethynylphenylamino)-6,7-bis(2-methoxy-ethoxy)-quinazolinium Methanesulfonate Using Near-Infrared Spectroscopy to Monitor Form Change Kinetics," *J. Chem. Soc., Perkin Trans.* 2000, vol. 2, pp. 2498-2502.

Onopchenko, et al., "Selective Catalytic Hydrogenation of Aromatic Nitro Groups in the Presence of Acetylenes. Synthesis of (3-Aminophenyl)acetylene via Hydrogenation of Dimethylcarbinol Substituted (3-Nitrophenyl)acetylene over Heterogeneous Metallic Ruthenium Catallyst," *Journal of Organic Chemistry* 1979, vol. 44, No. 8, pp. 1233-1236.

Pollack, V., et al., "Inhibition of Epidermal Growth Factor Receptor-Associated Tyrosine Phosphorylation in Human Carcinomas with CP-358,774: Dynamics of Receptor Inhibition In Situ and Antitumor Effects in Athymic Mice," *Journal of Pharmacology and Experimental Therapeutics*, 1999, vol. 291, No. 2, pp. 739-748.

Pollack et al., "Therapy of human Carcinomas in athymic mice by inhibition of EGF receptor-mediated signal transduction with CP-358774: Dynamics of receptor inhibition and anti-tumor effects" Proceedings of the Annual Meeting of the American Association for Cancer Research (1999) 291(2):739-748 (Abstract only).

Rosenberg, S., et al., "Studies Directed toward the Design of Orally Active Renin Inhibitors. 2. Development of the Efficacious, Bioavailable Renin Inhibitor (2S)-2-Benzyl-3-[[(1-methylpiperazin-4-yl)sulfonyl]propionyl]-3-thiazol-4-yl-L-alanine Amide of (2S, 3R, 4S)-2-Amino-1-cyclohexyl-3, 4-dihydroxy-6-methylheptane (A-72517)," *J. Med. Chem.* 1993, vol. 36, pp. 460-467.

Smaill, J., et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," *J. Med. Chem.* 2000, vol. 43, pp. 1380-1397.

Spurlock, C., "Increasing Solubility of Enoxacin and Norfloxacin by Means Salt Formation," *Journal of Parenteral Science and Technology* 1986, vol. 40, No. 2, pp. 70-72.

SMR Committee:"Protein Kinases: Therapeutic Opportunities" The Newsletter for the Society for Medicines Research (1999) 5(2):1-8.

Patent Abridgement of New Zealand patent No. NZ 0245662, filed Jan. 15, 1993.

Takalo, H., et al., "Synthesis of Some Substituted Dimethyl and Diethyl 4-(Phenylethynyl)-2,6-pyridine-dicarboxylates," *Acta Chemica Scandinavica*, vol. B42, pp. 448-454.

Trillo et al., (1993) Tratado de Farmacia Galencia, Primeria Edicion, pp. 81, 83, 84.

Sun Cunji et al., (1981) Yaoxue Xuebao 16(8): 564-570 C.A. 96 122727.

Watanabe M. et al., "Overexpression of Keratinocyte Growth Factor in Cancer Cells and Enterochromaffin Cells in Human Colorectal Cancer" (2000) Pathology International 50:363-372.

Woodburn J.R. et al., "ZD1839, An Epidermal Growth Factor Tyrosine Kinase Inhibitor Selected for Clinical Development" (1997) XP-001009911 (Abstract only).

TREATING ABNORMAL CELL GROWTH WITH A STABLE POLYMORPH OF N-(3-ETHYNYLPHENYL)-6,7-BIS(2-METHOXYETHOXY)-4-QUINAZOLINAMINE HYDROCHLORIDE

This application is a continuation of U.S. Ser. No. 09/711,272, filed Nov. 9, 2000, now U.S. Pat. No. 6,900,221, which claims the benefit of U.S. Provisional Application No. 60/206,420, filed May 23, 2000, U.S. Provisional Application No. 60/193,191, filed Mar. 30, 2000, and U.S. Provisional Application No. 60/164,907, filed Nov. 11, 1999, the contents of which are hereby incorporated by reference.

Throughout this application various publications are referenced. The disclosures of these publications in their entireties are hereby incorporated by reference into this application in order to more fully describe the state of the art to which this invention pertains.

BACKGROUND OF THE INVENTION

N-(3-ethynylphenyl)-6,7-bis (2-methoxyethoxy)-4-quinazolinamine, in either its hydrochloride or mesylate forms, or in an anhydrous and hydrous form, is useful in the treatment of hyperproliferative disorders, such as cancers, in mammals.

U.S. Pat. No. 5,747,498, issued May 5, 1998, which is incorporated herein by reference in its entirety, refers, in Example 20, to [6,7-bis(2-methoxyethoxy)-quinazolin-4-yl]-(3-ethynylphenyl)amine hydrochloride, which, the patent discloses, is an inhibitor of the erbB family of oncogenic and protooncogenic protein tyrosine kinases, such as epidermal growth factor receptor (EGFR), and is therefore useful for the treatment of proliferative disorders, such as cancers, in humans.

The mesylate form, described in PCT International Publication No. WO 99/55683 (PCT/IB99/00612, filed Apr. 8, 1999), the entire disclosure of which is incorporated herein by reference, and assigned to a common assignee, and shown in formula 1 below:

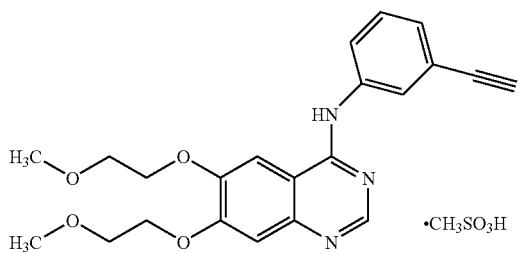

1 is useful for the treatment of proliferative disorders, and more preferred with parenteral methods of administration, as compared to the hydrochloride compound, i.e. with greater effectiveness in solution.

The mesylate compounds are more soluble in aqueous compositions than the hydrochloride compound, and thus the mesylate compounds are easily delivered according to parenteral methods of administration. The hydrochloride compound is however preferred with respect to solid administration such as with tablets and oral administration.

SUMMARY OF THE INVENTION

The present invention relates to polymorphs, and methods for the selective production of polymorphs of N-(3-ethynylphenyl)-6,7-bis(2-methoxyethoxy)-4-quinazolinamine hydrochloride, particularly in the stable polymorph form.

The present invention also relates to novel uses of N-(3-ethynylphenyl)-6,7-bis(2-methoxyethoxy)-4-quinazolinamine, in either its hydrochloride or mesylate forms, in an anhydrous or hydrous form, as well as in its various polymorph forms, in the treatment of hyperproliferative disorders, such as cancers, in mammals.

DETAILED DESCRIPTION OF THE INVENTION

Figure 1:
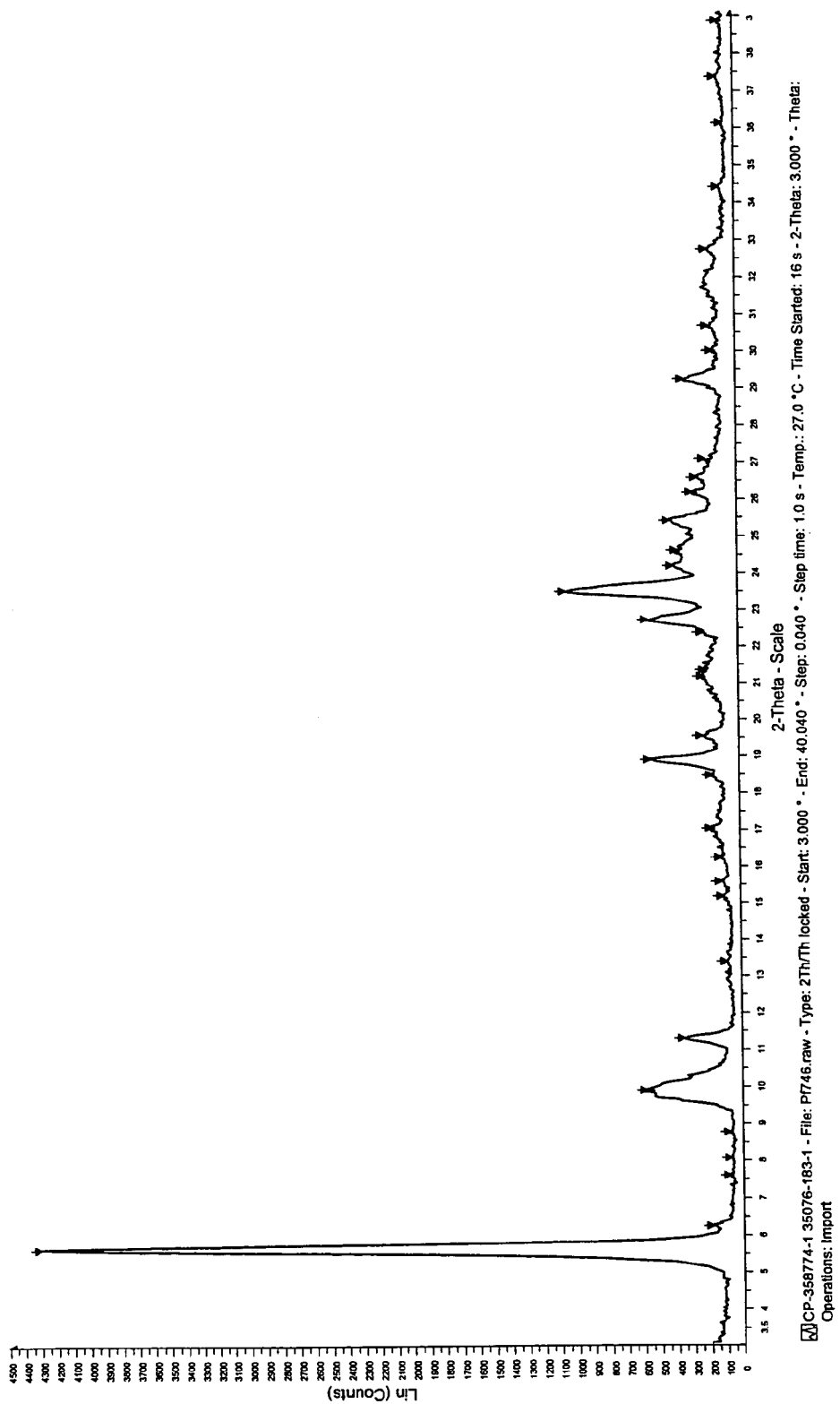
FIG. 1 The X-ray powder diffraction patterns for the hydrochloride polymorph A, the thermodynamically less stable form, over a larger range to show the first peaks.

Disclosed is a substantially homogeneous crystalline polymorph of the hydrochloride salt of N-(3-ethynylphenyl)-6,7-bis(2-methoxyethoxy)-4-quinazolinamine designated the B polymorph that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91. The polymorph is also characterized by the X-ray powder diffraction pattern shown in FIG. 3.

Disclosed is a crystalline polymorph of the hydrochloride salt of N-(3-ethynylphenyl)-6,7-bis(2-methoxyethoxy)-4-quinazolinamine designated the B polymorph that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91, which is substantially free of the polymorph designated the A polymorph. The polymorph is also characterized by the X-ray powder diffraction pattern shown in FIG. 3.

The polymorph designated the B polymorph may be in substantially pure form, relative to the A polymorph.

Also disclosed is a composition comprising a substantially homogeneous crystalline polymorph of the hydrochloride salt of N-(3-ethynylphenyl)-6,7-bis(2-methoxyethoxy)-4-quinazolinamine that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91. The hydrochloride salt of N-(3-ethynylphenyl)-6,7-bis (2-methoxyethoxy)-4-quinazolinamine also exhibits an X-ray powder diffraction pattern having characteristic peaks expressed in degrees 2-theta at approximately the values show in Table 3 or in Table 4 below. And, the N-(3-ethynylphenyl)-6,7-bis(2-methoxyethoxy)-4-quinazolinamine hydrochloride in the polymorph B form may characterized by the X-ray powder diffraction pattern shown in FIG. 3.

Also disclosed is a composition comprising a crystalline polymorph of the hydrochloride salt of N-(3-ethynylphenyl)-6,7-bis(2-methoxyethoxy)-4-quinazolinamine designated the B polymorph that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91 in a weight % of the B polymorph relative to the A polymorph which is at least 70%. This composition may comprise at least 75% polymorph B, by weight; at least 80% polymorph B, by weight; at least 85% polymorph B, by weight; at least 90% polymorph B, by weight; at least 95% polymorph B, by weight; at least 97% polymorph B, by weight; at least 98% polymorph B, by weight; or at least 99% polymorph B, by weight relative to the A polymorph.

Further disclosed is a process for producing the polymorph B of the hydrochloride salt of N-(3-ethynylphenyl)-6,7-bis(2-methoxyethoxy)-4-quinazolinamine by recrystallization of N-(3-ethynylphenyl)-6,7-bis(2-methoxyethoxy)-4-quinazolinamine hydrochloride in a solvent comprising alcohol and water.

In the process, the recrystallization may comprise the steps of:
a) heating to reflux alcohol, water and the hydrochloride salt of N-(3-ethynylphenyl)-6,7-bis(2-methoxyethoxy)-4-quinazolinamine so as to form a solution;
b) cooling the solution to between about 65 and 70° C.;
c) clarifying the solution; and
d) precipitating polymorph B by further cooling the clarified solution.

In the process, the N-(3-ethynylphenyl)-6,7-bis(2-methoxyethoxy)-4-quinazolinamine hydrochloride is prepared by the steps of:
coupling a compound of formula 6

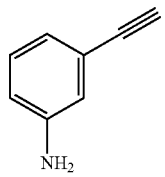

6 with a compound of formula 4

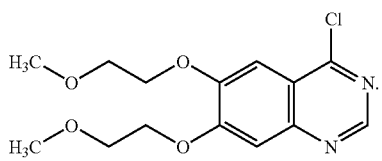

4

The compound of formula 6 is prepared by reacting a compound of formula formula 5

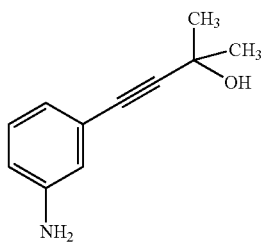

5 in a suspension of metal alkali and solvent and with heating.
The compound of formula 4 is prepared by chlorinating a compound of formula 3

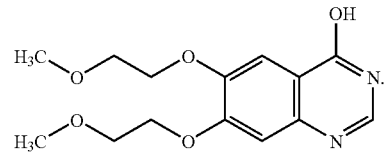

3

Also disclosed is a pharmaceutical composition for the treatment of a hyperproliferative disorder in a mammal which substantially comprises a therapeutically effective amount of the polymorph B and a pharmaceutically acceptable carrier.

The pharmaceutical composition may be adapted for oral administration. It may be in the form of a tablet.

Also disclosed is a method of treating a hyperproliferative disorder in a mammal which comprises administering to said mammal a therapeutically effective amount of the polymorph B.

The method may be for the treatment of a cancer selected from brain, squamous cell, bladder, gastric, pancreatic, breast, head, neck, oesophageal, prostate, colorectal, lung, renal, kidney, ovarian, gynecological and thyroid cancer.

The method may also be for the treatment of a cancer selected from non-small cell lung cancer (NSCLC), refractory ovarian cancer, head and neck cancer, colorectal cancer and renal cancer.

In the method, the therapeutically effective amount may be from about 0.001 to about 100 mg/kg/day, or from about 1 to about 35 mg/kg/day.

In the method, the therapeutically effective amount may also be from about 1 to about 7000 mg/day; from about 5 to about 2500 mg/day; from about 5 to about 200 mg/day; or from about 25 to about 200 mg/day.

Further disclosed is a method for the treatment of a hyperproliferative disorder in a mammal which comprises administering to said mammal a therapeutically effective amount of the polymorph B in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

Yet further disclosed is a method of making a composition which composition comprises substantially homogeneous crystalline polymorph of the hydrochloride salt of N-(3-ethynylphenyl)-6,7-bis(2-methoxyethoxy)-4-quinazolinamine designated the B polymorph that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91, comprising admixing the crystalline polymorph desigated the B polymorph with a carrier.

The carrier may be a pharmaceutically acceptable carrier.

Also disclosed is a method of preparing polymorph B of N-(3-ethynylphenyl)-6,7-bis(2-methoxyethoxy)-4-quinazolinamine hydrochloride which comprises the step of recrystallizing N-(3-ethynylphenyl)-6,7-bis (2-methoxyethoxy)-4-quinazolinamine hydrochloride in a solvent comprising alcohol.

In the method the solvent may further comprises water.

In the method, the N-(3-ethynylphenyl)-6,7-bis (2-methoxyethoxy)-4-quinazolinamine hydrochloride is prepared by coupling a compound of formula 6

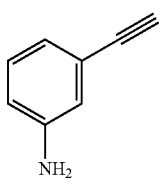

with a compound of formula 4

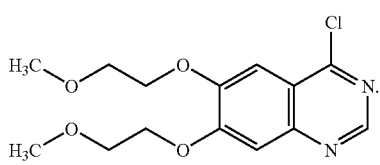

In the method, the compound of formula 6 is prepared by reacting a compound of formula 5

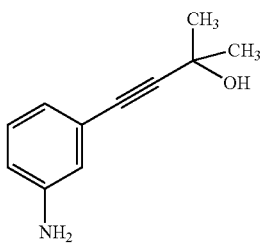

in a suspension of metal alkali and solvent and with heating.

In the method, the compound of formula 4 is prepared by chlorinating a compound of formula 3

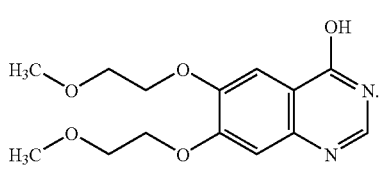

Further disclosed is a method for the production of the polymorph B of claim 1 comprising the steps of:

a) substitution chlorination of starting quinazolinamine compound of formula 3

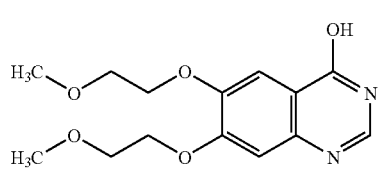

having an hydroxyl group, to provide a compound of formula 4

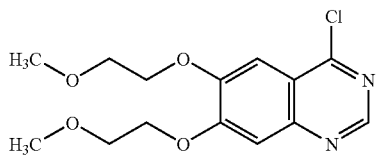

by reaction thereof in a solvent mixture of thionyl chloride, methylene chloride and dimethylformamide, b) preparation of a compound of formula 6

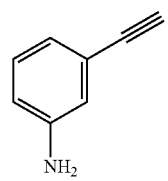

in situ from starting material of compound of formula 5

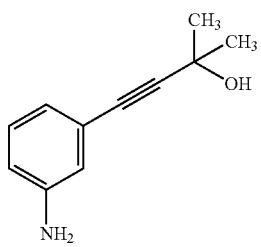

by reaction of the latter in a suspension of metal alkali and solvent and with heating;

c) reaction of the compound of formula 6 in situ with the compound of formula 4 wherein the compound of formula 6 replaces the chlorine in the compound of formula 4 to give the N-(3-ethynylphenyl)-6,7-bis(2-methoxyethoxy)-4-quinazolinamine hydrochloride;

d) recrystallizing the N-(3-ethynylphenyl)-6,7-bis(2-methoxyethoxy)-4-quinazolinamine hydrochloride, in alcohol, into the polymorph B form.

In this method, the substitution chlorination may be quenched in the presence of aqueous sodium hydroxide; aqueous sodium bicarbonate; aqueous potassium hydroxide; aqueous potassium bicarbonate; aqueous potassium carbonate; aqueous sodium carbonate, or a mixture thereof.

Yet further disclosed is a method for the production of polymorph B of the hydrochloride salt of N-(3-ethynylphenyl)-6,7-bis(2-methoxyethoxy)-4-quinazolinamine by recrystallization comprising the steps of:

a) heating to reflux alcohol, water and the hydrochloride salt of N-(3-ethynylphenyl)-6,7-bis (2-methoxyethoxy)-4-quinazolinamine so as to form a solution;

b) cooling the solution to between about 65 and 70° C.;

c) clarifying the solution; and d) precipitating polymorph B by further cooling the clarified solution.

Further disclosed is a composition consisting essentially of N-(3-ethynylphenyl)-6,7-bis(2-methoxyethoxy)-4-quinazolinamine hydrochloride in the form of polymorph A, which is characterized by the following peaks in its X-ray powder diffraction pattern shown in FIG. 1.

Also disclosed is a composition consisting essentially of N-(3-ethynylphenyl)-6,7-bis(2-methoxyethoxy)-4-quinazolinamine hydrochloride in the form of polymorph A, which is characterized by the peaks shown is Table 1 or Table 2 below.

A prodrug of any of the compound herein is also disclosed.

Further disclosed is a method of inducing differentiation of tumor cells in a tumor comprising contacting the cells with an effective amount of any of the compounds or compositions disclosed herein.

Also discosed is a method for the treatment of NSCLC (non small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases and atherosclerosis in a mammal comprising administering to said mammal a therapeutically effective amount of a pharmaceutical composition comprised of at least one of N-(3-ethynylphenyl)-6,7-bis(2-methoxyethoxy)-4-quinazolinamine, and pharmaceutically acceptable salts thereof in anhydrous and hydrate forms.

The treatment may further comprise a palliative or neo-adjuvant/adjuvant monotherapy; or comprises blocking epidermal growth factor receptors (EGFR).

The method of may also be used in the treatment of tumors that express EGFRvIII.

The method may further comprise a combination with any of chemotherapy and immunotherapy; or treatment with either or both anti-EGFR and anti-EGF antibodies; or administration to said mammal of a member of the group consisting of inhibitors of MMP (matrix-metallo-proteinase), VEGFR (vascular endothelial growth factor receptor), farnesyl transferase, $CTLA_4$. (cytotoxic T-lymphocyte antigen 4) and erbB2, MAb to VEGFr, rhuMAb-VEGF, erbB2 MAb and avb3 Mab.

The pharmaceutical compounds used may be radiation sensitizers for cancer treatment or in combination with anti-hormonal therapies, or for the inhibition of tumor growth in humans in a regimen with radiation treatment.

Further disclosed is a method for the chemoprevention of basal or squamous cell carcinoma of the skin in areas exposed to the sun or in persons of high risk to said carcinoma, said method comprising administering to said persons a therapeutically effective amount of a pharmaceutical composition comprised of at least one of N-(3-ethynylphenyl)-6,7-bis(2-methoxyethoxy)-4-quinazolinamine, and pharmaceutically acceptable salts thereof in anhydrous and hydrate forms.

Also is a method of inducing differentiation of tumor cells in a tumor comprising contacting the cells with an effective amount of the compound of at least one of N-(3-ethynylphenyl)-6,7-bis(2-methoxyethoxy)-4-quinazolinamine, and pharmaceutically acceptable salts thereof in anhydrous and hydrate forms.

It is accordingly an object of the present invention to provide a method for the production of the hydrochloride salt of N-(3-ethynylphenyl)-6,7-bis(2-methoxyethoxy)-4-quinazolinamine in HCl form (Formula 2):

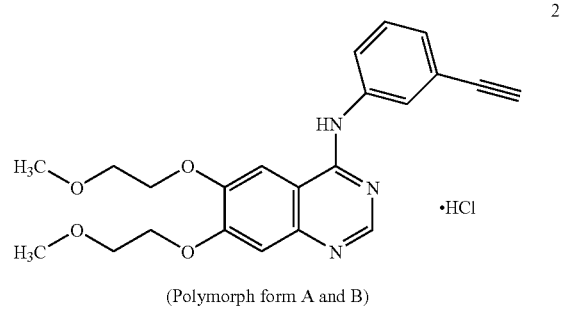

(Polymorph form A and B)

making it more suitable for tablet and oral administration and consisting essentially of the stable polymorphic form (polymorph form B) as well as the compound in such polymorph B form and the intermediate polymorph A in essentially pure form.

It is a further object of the present invention to provide such stable polymorph form B in a pharmaceutical orally administered composition.

Stability of the hydrochloride compound is of concern for its use in the treatment of patients since variations will affect effective dosage level and administration. It has been discovered that the hydrochloride of N-(3-ethynylphenyl)-6,7-bis(2-methoxyethoxy)-4-quinazolinamine exists in two polymorph states, polymorph A and B. This contrasts with the mesylate compounds which exist in three polymorph states (mesylate polymorphs A, B and C). Polymorph B of the hydrochloride was found to be the thermodynamically most stable and desirable form and the present invention comprises the polymorph B compound in the substantially pure polymorphic B form and pharmaceutical compositions of the substantially pure form of polymorph B, particularly in tablet form and a method of the selective production of the compound.

The hydrochloride compound disclosed in the U.S. Pat. No. 5,747,498 actually comprised a mixture of the polymorphs A and B, which, because of its partially reduced stability (i.e., from the polymorph A component) was not more preferred for tablet form than the mesylate salt forms.

Figure 2:
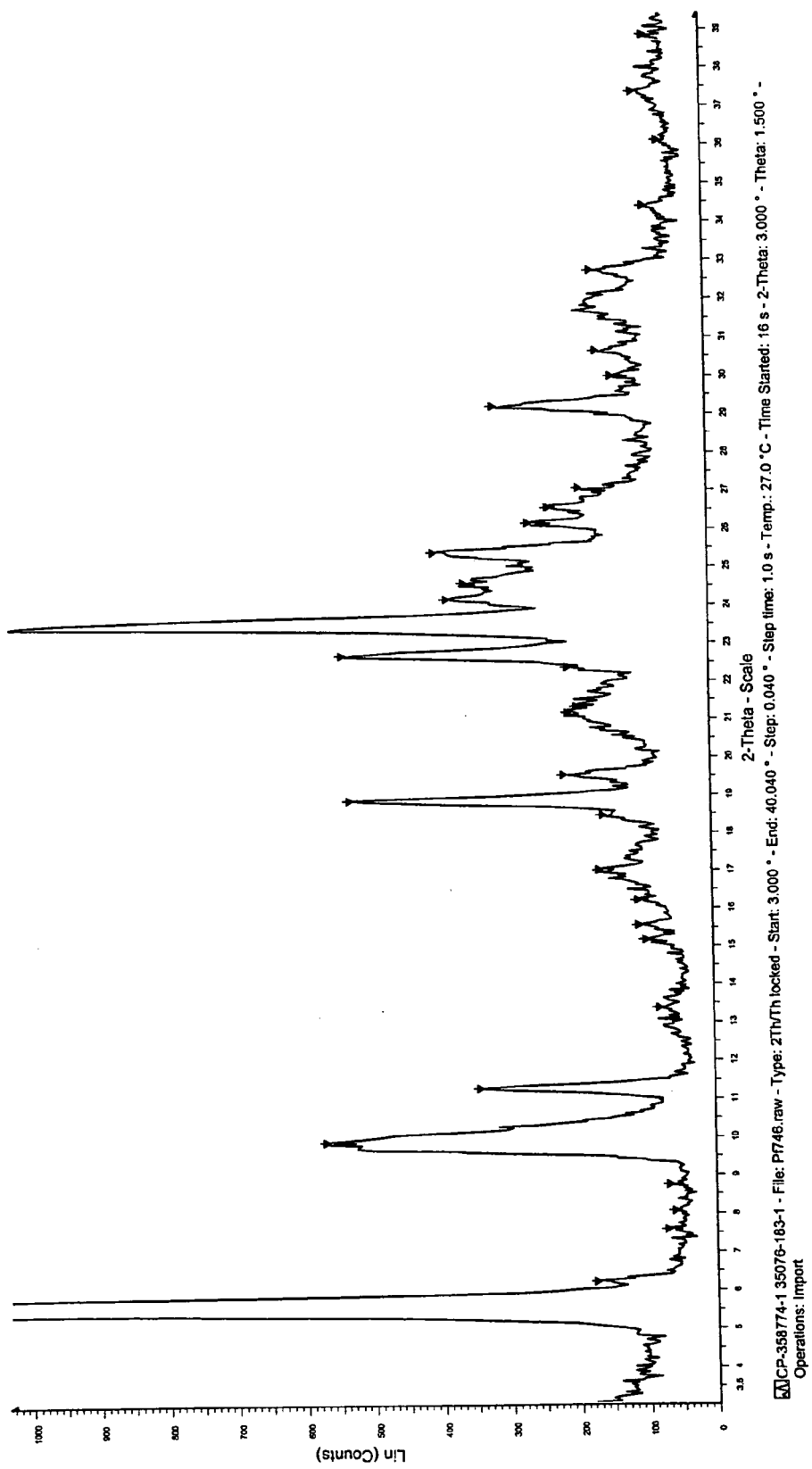
FIG. 2 The X-ray powder diffraction patterns for the hydrochloride polymorph A, the thermodynamically less stable form, are over a shorter range to show more detail.
Figure 3:
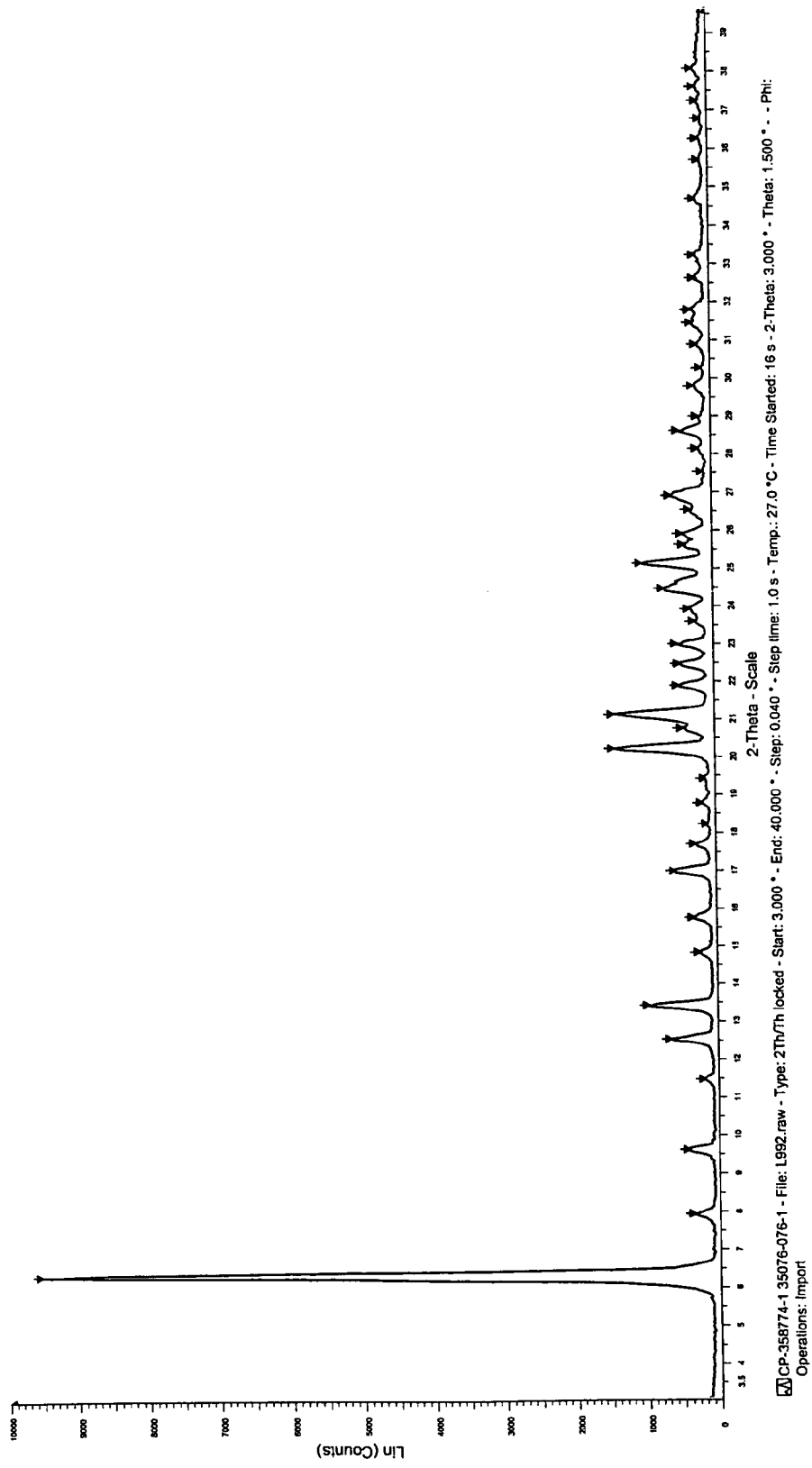
FIG. 3 The X-ray powder diffraction patterns for the hydrochloride polymorph B, the thermodynamically more stable form, over a larger range to show the first peaks.
Figure 4:
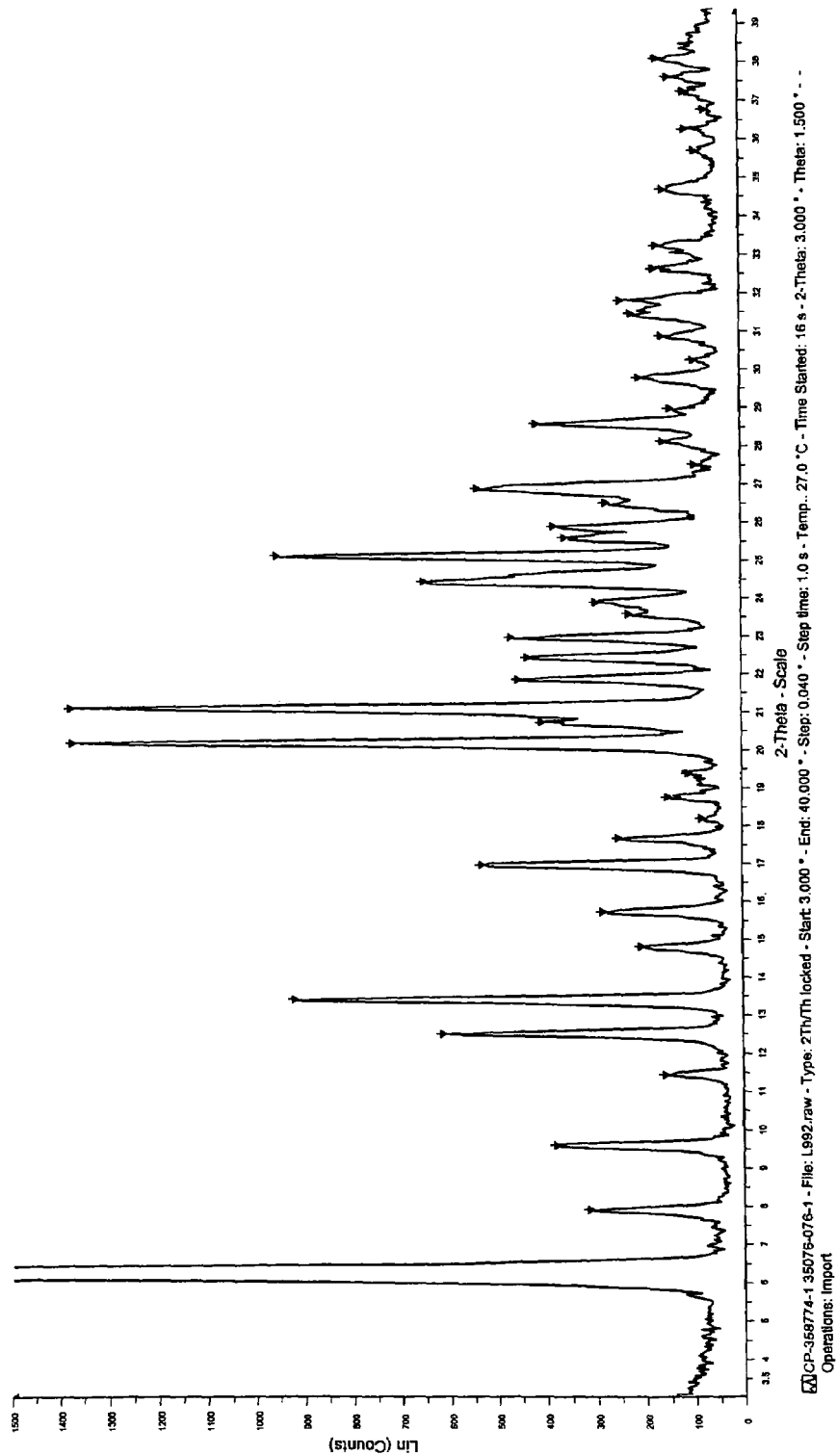
FIG. 4 The X-ray powder diffraction patterns for the hydrochloride polymorph B, the thermodynamically more stable form, over a shorter range to show more detail.

Specifically, the present invention relates to methods of producing the hydrochloride compound forms of N-(3-ethynylphenyl) -6,7-bis(2-methoxyethoxy)-4-quinazolinamine and for producing the stable form B in high yield. The mesylate salt of N-(3-ethynylphenyl)-6,7-bis (2-methoxyethoxy)-4-quinazolinamine has been discovered to exist in at least three polymorphic forms which have been designated A, B, and C, of increasing stability with different X-ray powder diffraction patterns. The X-ray powder diffraction patterns for the hydrochloride polymorph A ($A_1$ and $A_2$) and B ($B_1$ and $B_2$) forms are shown in FIGS. 1–4 as follows: graphs of FIGS. 1 and 3 are over a larger range to fully show the first peaks for A and B, respectively, and graphs of FIGS. 2 and 4 are over a shorter range to show more overall detail for A and B, respectively.

The data contained in the above X-ray diffraction patterns of FIG. 1–4 are tabulated in the following Tables 1–4:

TABLE 1

Polymorph A
Anode: Cu - Wavelength 1: 1.54056 Wavelength 2: 1.54439
(Rel Intensity: 0.500)
Range# 1 - Coupled: 3.000 to 40.000 StepSize: 0.040
StepTime: 1.00
Smoothing Width: 0.300 Threshold: 1.0

| d(A) | I(rel) |
| --- | --- |
| 15.82794 | 100.0 |
| 14.32371 | 3.9 |
| 11.74376 | 1.5 |
| 11.03408 | 1.2 |
| 10.16026 | 1.4 |
| 8.98039 | 13.1 |
| 7.85825 | 7.8 |
| 6.63179 | 1.7 |
| 5.84901 | 2.1 |
| 5.69971 | 2.3 |
| 5.46922 | 2.4 |
| 5.21396 | 3.6 |
| 4.80569 | 3.5 |
| 4.70077 | 12.2 |
| 4.54453 | 4.8 |
| 4.19685 | 4.7 |
| 4.16411 | 4.4 |
| 3.97273 | 4.7 |
| 3.91344 | 12.4 |
| 3.78223 | 24.2 |
| 3.67845 | 8.8 |
| 3.61674 | 8.2 |
| 3.50393 | 9.3 |
| 3.40200 | 6.0 |
| 3.35174 | 5.3 |
| 3.29005 | 4.2 |
| 3.05178 | 7.1 |
| 2.97750 | 3.0 |
| 2.91238 | 3.5 |
| 2.73148 | 3.7 |
| 2.60193 | 1.8 |
| 2.48243 | 1.3 |
| 2.40227 | 2.2 |
| 2.31297 | 1.7 |

TABLE 2

Polymorph A
Anode: Cu - Wavelength 1: 1.54056 Wavelength 2: 1-54439
(Rel Intensity: 0.500)
Range#1 - Coupled: 3.000 to 40.000 StepSize: 0.040
StepTime: 1.00
Smoothing Width: 0.300 Threshold: 1.0

| 2-Theta | I(rel) |
| --- | --- |
| 5.579 | 100.0 |
| 6.165 | 3.9 |
| 7.522 | 1.5 |
| 8.006 | 1.2 |
| 8.696 | 1.4 |
| 9.841 | 13.1 |
| 11.251 | 7.8 |
| 13.340 | 1.7 |
| 15.135 | 2.1 |
| 15.534 | 2.3 |
| 16.193 | 2.4 |
| 16.991 | 3.6 |
| 18.447 | 3.5 |
| 18.862 | 12.2 |
| 19.517 | 4.8 |
| 21.152 | 4.7 |
| 21.320 | 4.4 |
| 22.360 | 4.7 |
| 22.703 | 12.4 |
| 23.502 | 24.2 |
| 24.175 | 8.8 |
| 24.594 | 8.2 |
| 25.398 | 9.3 |
| 26.173 | 6.0 |
| 26.572 | 5.3 |
| 27.080 | 4.2 |
| 29.240 | 7.1 |
| 30.007 | 3.0 |
| 30.673 | 3.5 |
| 32.759 | 3.7 |
| 34.440 | 1.8 |
| 36.154 | 1.3 |
| 37.404 | 2.2 |
| 38.905 | 1.7 |

TABLE 3

Polymorph B
Anode: Cu - Wavelength 1 1.54056 Wavelength 2: 1.54439
(Rel Intensity: 0.500)
Range # 1 - Coupled 3.000 to 40.040 StepSize: 0.040
StepTime 1.00
Smoothing Width: 0.300 Threshold: 1.0

| d(A) | I(rel) |
| --- | --- |
| 14.11826 | 100.0 |
| 11.23947 | 3.2 |
| 9.25019 | 3.9 |
| 7.74623 | 1.5 |
| 7.08519 | 6.4 |
| 6.60941 | 9.6 |
| 5.98828 | 2.1 |
| 5.63253 | 2.9 |
| 5.22369 | 5.5 |
| 5.01567 | 2.5 |
| 4.87215 | 0.7 |
| 4.72882 | 1.5 |
| 4.57666 | 1.0 |
| 4.39330 | 14.4 |
| 4.28038 | 4.2 |
| 4.20645 | 14.4 |
| 4.06007 | 4.7 |
| 3.95667 | 4.5 |
| 3.86656 | 4.8 |
| 3.76849 | 2.3 |
| 3.71927 | 3.0 |
| 3.63632 | 6.8 |
| 3.53967 | 10.0 |
| 3.47448 | 3.7 |
| 3.43610 | 3.9 |
| 3.35732 | 2.8 |
| 3.31029 | 5.6 |
| 3.23688 | 0.9 |
| 3.16755 | 1.5 |
| 3.11673 | 4.3 |
| 3.07644 | 1.4 |
| 2.99596 | 2.1 |
| 2.95049 | 0.9 |
| 2.89151 | 1.6 |
| 2.83992 | 2.2 |
| 2.81037 | 2.4 |
| 2.74020 | 1.7 |
| 2.69265 | 1.7 |
| 2.58169 | 1.5 |
| 2.51043 | 0.8 |
| 2.47356 | 1.0 |
| 2.43974 | 0.6 |
| 2.41068 | 1.1 |
| 2.38755 | 1.4 |
| 2.35914 | 1.7 |

TABLE 4

Polymorph B
Anode: Cu - Wavelength 1 1.54056 Wavelength 2: 1.54439
(Rel Intensity: 0.500)
Range# 1 - Coupled: 3.000 to 40.040 StepSize 0.040
StepTime: 1.00
Smothing Width: 0.300 Threshold: 1.0

| 2-Theta | I(rel) |
| --- | --- |
| 6.255 | 100.0 |
| 7.860 | 3.2 |
| 9.553 | 3.9 |
| 11.414 | 1.5 |
| 12.483 | 6.4 |
| 13.385 | 9.6 |
| 14.781 | 2.1 |
| 15.720 | 2.9 |
| 16.959 | 5.5 |
| 17.668 | 2.5 |
| 18.193 | 0.7 |
| 18.749 | 1.5 |
| 19.379 | 1.0 |
| 20.196 | 14.4 |
| 20.734 | 4.2 |
| 21.103 | 14.4 |
| 21.873 | 4.7 |
| 22.452 | 4.5 |
| 22.982 | 4.8 |
| 23.589 | 2.3 |
| 23.906 | 3.0 |
| 24.459 | 6.8 |
| 25.138 | 10.0 |
| 25.617 | 3.7 |
| 25.908 | 3.9 |
| 26.527 | 2.8 |
| 26.911 | 5.6 |
| 27.534 | 0.9 |
| 28.148 | 1.5 |
| 28.617 | 4.3 |
| 29.000 | 1.4 |
| 29.797 | 2.1 |
| 30.267 | 0.9 |
| 30.900 | 1.6 |
| 31.475 | 2.2 |
| 31.815 | 2.4 |
| 32.652 | 1.7 |
| 33.245 | 1.7 |
| 34.719 | 1.5 |
| 35.737 | 0.8 |
| 36.288 | 1.0 |
| 36.809 | 0.6 |
| 37.269 | 1.1 |
| 37.643 | 1.4 |
| 38.114 | 1.7 |

It is to be understood that the X-ray powder diffraction pattern is only one of many ways to characterize the arrangement of atoms comprising the compound N-(3-ethynylphenyl)-6,7-bis(2-methoxyethoxy)-4-quinazolinamine hydrochloride, and that other methods well known in the art, e.g. single crystal X-ray diffraction, may be used to identify in a sample, composition or other preparation the presence of polymorph B of the hydrochloride salt of N-(3-ethynylphenyl)-6,7-bis(2-methoxyethoxy)-4-quinazolinamine.

The present invention relates to a compound which is polymorph B of the hydrochloride salt of N-(3-ethynylphenyl)-6,7-bis(2-methoxyethoxy)-4-quinazolinamine that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91. This invention also relates to a polymorph of the hydrochloride salt of N-(3-ethynylphenyl)-6,7-bis (2-methoxyethoxy)-4-quinazolinamine that exhibits an X-ray powder diffraction pattern having characteristic peaks expressed in degrees 2-theta at approximately the values shown in Table 4 above.

This invention also relates to a compound which is polymorph A of the hydrochloride salt of N-(3-ethynylphenyl)-6,7-bis(2-methoxyethoxy)-4-quinazolinamine that exhibits an X-ray powder diffraction pattern having characteristic peaks expressed in degrees 2-theta at approximately 5.58, 9.84, 11.25, 18.86, 22.70, 23.50, 24.18, 24.59, 25.40 and 29.24. This invention also relates to a polymorph of the hydrochloride salt of N-(3-ethynylphenyl)-6,7-bis(2-methoxyethoxy)-4-quinazolinamine that exhibits an X-ray powder diffraction pattern having characteristic peaks expressed in degrees 2-theta at approximately the values shown in Table 2 above.

Method of Production

The polymorph B in substantially pure form of N-(3-ethynylphenyl)-6,7-bis (2-methoxyethoxy)-4-quinazolinamine hydrochloride (compound of formula 1) is prepared, in accordance with the method of the present invention, by the steps of;

1) substitution chlorination of starting quinazolinamine compound (formula 3):

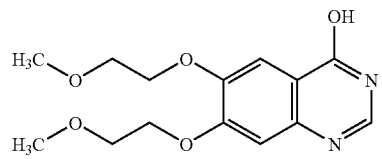

3 having an hydroxyl group, such as by reaction thereof in a solvent mixture of thionyl chloride, methylene chloride, and dimethylformamide, and finally quenching the reaction with an aqueous solution of sodium hydroxide or sodium bicarbonate. The compound of formula 4:

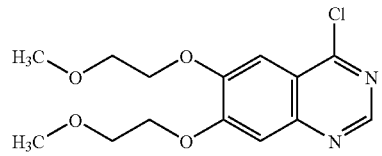

4 is produced in high yield with replacement of the hydroxyl group with chlorine;

2) preparation of compound of formula 6:

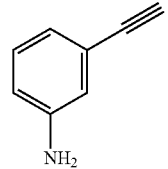

6 from starting material of formula 5:

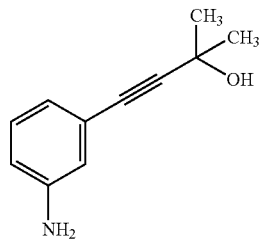

5 by reaction of the latter in a suspension of NaOH (or KOH, or a combination) in toluene with heating;

3) reaction of the compound of formula 6 with the compound of formula 4 of step 1 wherein the compound of formula 6 replaces the chlorine to give the N-(3-ethynylphenyl)-6,7-bis(2-methoxyethoxy) -4-quinazolinamine hydrochloride (compound of formula 2) with a. 97% yield.

4) recrystallization of the compound of formula 2 (comprising both polymorph A and polymorph B) into the more stable polymorph B in a solvent comprising alcohol (e.g. 2B-ethanol) and water, generally in high yield, e.g., about 85%.

Accordingly, the present invention relates to a method of preparing polymorph B of N-(3-ethynylphenyl)-6,7-bis(2-methoxyethoxy)-4-quinazolinamine hydrochloride which comprises recrystallization of N-(3-ethynylphenyl)-6,7-bis (2-methoxyethoxy) -4-quinazolinamine hydrochloride in a solvent comprising alcohol and water. In one embodiment, the method comprises the steps of heating to reflux alcohol, water and the hydrochloride salt of N-(3-ethynylphenyl)-6,7-bis (2-methoxyethoxy)-4-quinazolinamine so as to form a solution; cooling the solution to between about 65 and 70° C.; clarifying the solution; and precipitating polymorph B by further cooling the clarified solution. In an embodiment, the alcohol is ethanol. In a preferred embodiment, the ratio of ethanol to water is about 4:1. It is to be expected that other lower alcohols, e.g., $C_1$–$C_4$ alcohols, are also suitable for recrystallization of polymorph B with adjustment of the alcohol to water ratio as needed. In another preferred embodiment, the compound to be recrystallized is present in an amount relative to the total volume of solvent at a weight to volume ratio of about 0.05. In an embodiment, N-(3-ethynylphenyl)-6,7-bis(2-methoxyethoxy)-4-quinazolinamine hydrochloride is prepared by coupling a compound of formula 6 with a compound of formula 4. In another embodiment, the compound of formula 6 is prepared by reacting a compound of formula 5 in a suspension of metal alkali and solvent, with heating.

In an embodiment, the compound of formula 4 is prepared by chlorinating a compound of formula 3 by reaction of the latter in a solvent mixture of thionyl chloride, methylene chloride and dimethylformide, and subsequently quenching the reaction with an aqueous solution of sodium hydroxide. Alternatively, an aqueous solution of sodium bicarbonate can be substituted for the sodium hydroxide solution.

This invention relates to polymorph B of the hydrochloride salt of N-(3-ethynylphenyl)-6,7-bis(2-methoxyethoxy)-4-quinazolinamine prepared by the above methods. In an embodiment, the polymorph B is prepared by using the starting materials described herein. In a preferred embodiment, polymorph B is prepared by reaction of the starting materials described herein with the reagents and conditions according to the methods described herein and in the Examples which follow.

General Synthesis

N-(3-ethynylphenyl)-6,7-bis(2-methoxyethoxy)-4-quinazolinamine hydrochloride has been found to exist in two distinct anhydrous polymorphic forms A and B. The production method for the various polymorphs is with components separately reacted in accordance with the following scheme:

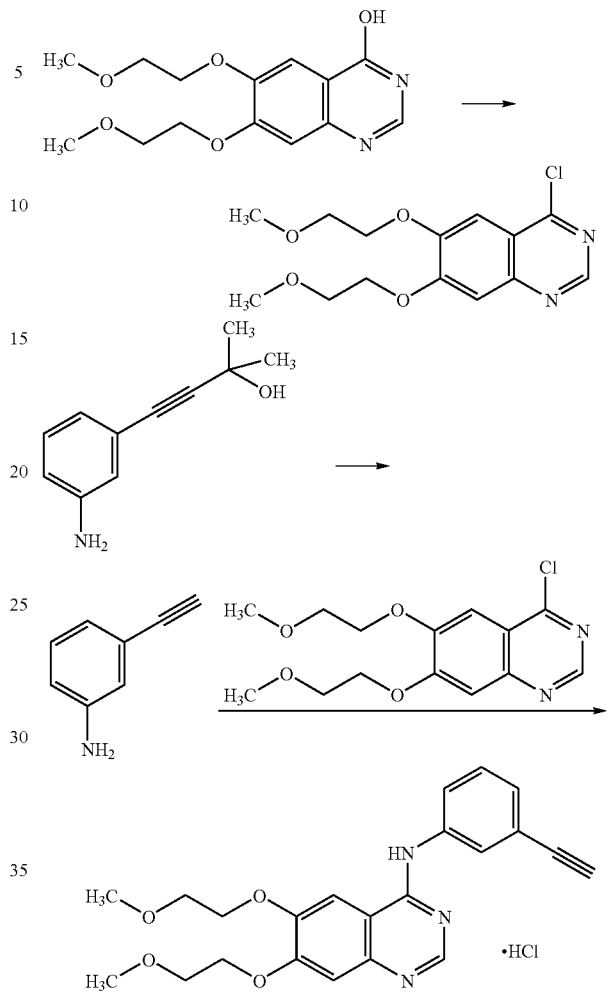

Uses

As described in the aforementioned U.S. Pat. No. 5,747,498 and PCT International Publication No. WO 99/55683, the compounds made in accordance with the present invention are useful for the treatment of a hyperproliferative disorder in a mammal which comprises a therapeutically effective amount of the hydrochloride or mesylate form of N-(3-ethynylphenyl)-6,7-bis(2-methoxyethoxy) -4-quinazolinamine, and a pharmaceutically acceptable carrier.

The term "compound(s) of the invention" referred to herein is preferably the polymorph B form of the hydrochloride salt of N-(3-ethynylphenyl)-6,7-bis(2-methoxyethoxy)-4-quinazolinamine hydrochloride, but is not meant to exclude the mesylate form and its three polymorphs, or polymorph A of the hydrochloride form, or a mixture of polymorphs B and A of the hydrochloride form or other non-crystalline forms of the compound.

The term "treating" as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restenosis. "Abnormal cell growth" as used herein also refers to and includes the abnormal growth of cells, both benign and malignant, resulting from activity of the enzymes farnesyl protein transferase, protein kinases, protein phosphatases, lipid kinases, lipid phosphatases, or activity or trascription factors, or intracellular or cell surface receptor proteins.

[6,7-bis(2-methoxyethoxy)quinazolin-4-yl]-(3-ethynylphenyl)-amine hydrochloride, preferably the stable polymorph B form, is additionally used for the treatment of a variety of additional human tumors containing hyperproliferating cells that are activated by the signal transduction pathways stimulated by EGFR, whether by overexpression (e.g. due to one or more of—altered transcription, altered mRNA degradation or gene amplification) of the EGFR protein itself, another receptor protein with which EGFR can form active heterodimers, or one of the ligands that activate EGFR (e.g. EGF, TGFα, amphiregulin, β-cellulin, heparin-binding EGF, or epiregulin) or a heterodimerizing receptor, or due to a dependence or partial dependence on the activity of a "normal" level of EGFR protein, whether activated by extracellular ligand, intracellular signal transduction pathways and/or genetic alterations or polymorphisms that result in amino acid substitutions that produce increased or ligand-independent activity (e.g. EGFRvIII, Archer G. E. et. al. (1999) Clinical Cancer Research 5:2646–2652). Such tumors, including both benign and malignant, include renal (such as kidney, renal cell carcinoma, or carcinoma of the renal pelvis), liver, kidney, bladder (particularly invasive tumors), breast (including estrogen receptor negative and positive tumors, and progesterone receptor negative and positive tumors), gastric, esophageal (including Barrett's mucosa, squamous cell carcinomas and adenocarcinomas), larynx, ovarian, colorectal (particularly deeply invasive tumors), including anal, prostate, pancreatic, lung (particularly non-small cell lung cancer (NSCLC) adenocarcinomas, large cell tumors and squamous cell carcinomas, but also reactive (squamous metaplasia and inflammatory atypia) as well as precancerous (dysplasia and carcinoma in situ) bronchial lesions associated with both NSCLC adenocarcinomas and squamous cell carcinomas), gynecological, including vulval, endometrial, uterine (e.g, sarcomas), cervical, vaginal, vulval, and fallopian tube cancers, thyroid, hepatic carcinomas, skin cancers, sarcomas, brain tumors, including glioblastomas (including gliobastoma multiforme), astrocytomas, schwanomas, ependymonas, medulloblastomas, meningiomas and pituitary adenomas, and various other head and neck tumors (particularly squamous cell carcinomas), and metastases of all of the above.

[6,7-bis(2-methoxyethoxy)quinazolin-4-yl]-(3-ethynylphenyl)-amine hydrochloride, preferably the stable polymorph B form, is also used for the treatment of a variety of additional human hyperplastic conditions containing hyperproliferating cells that are activated by the signal transduction pathways capable of stimulation by EGFR, such as benign hyperplasia of the skin (e.g. psoriasis) or prostate (e.g. BPH), chronic pancreatitis, or reactive hyperplasia of pancreatic ductal epithelium, or kidney disease (including proliferative glomerulonephritis and diabetes-induced renal disease) in a mammal which composition comprises a therapeutically effective amount of the hydrochloride of N-(3-ethynylphenyl)-6,7-bis(2-methoxyethoxy)-4-quinazolinamine, preferably the polymorph B form, and a pharmaceutically acceptable carrier.

In addition, pharmaceutical compositions including the compounds made in accordance with the present invention provide for the prevention of blastocyte implantation in a mammal, which composition comprises a therapeutically effective amount of N-(3-ethynylphenyl)-6,7-bis(2-methoxyethoxy)-4-quinazolinamine hydrochloride, preferably the polymorph B form, and a pharmaceutically acceptable carrier.

[6,7-bis (2-methoxyethoxy) quinazolin-4-yl]-(3-ethynylphenyl)-amine hydrochloride, preferably the stable polymorph B form, is also used for the treatment of additional disorders in which cells are activated by the signal transduction pathways stimulated by EGFR, whether by overexpression (due to one or more of—altered transcription, altered mRNA degradation or gene amplification) of the EGFR protein itself, another receptor protein with which it can form active heterodimers, or one of the ligands that activate EGFR (e.g. EGF, TGFα, amphiregulin, β-cellulin, heparin-binding EGF, or epiregulin) or a heterodimerizing receptor, or due to a dependence or partial dependence on the activity of a "normal" level of EGFR protein, whether activated by extracellular ligand, intracellular signal transduction pathways and/or genetic alterations or polymorphisms that result in amino acid substitutions that produce increased or ligand-independent activity (e.g. EGFRvIII, Archer G. E. et. al. (1999) Clinical Cancer Research 5:2646–2652). Such disorders may include those of a neuronal, glial, astrocytal, hypothalamic, and other glandular, macrophagal, epithelial, stromal, or blastocoelic nature in which aberrant or 'normal' function, expression, activation or signalling via EGFR may be involved. Such disorders may furthermore involve the modulation by EGF (or other ligands that activate EGFR or heterodimerizing receptors) of adipocyte lipogenesis, bone resorption, hypothalamic CRH release, hepatic fat accumulation, T-cell proliferation, skin tissue proliferation or differentiation, corneal epithelial tissue proliferation or differentiation, macrophage chemotaxis or phagocytosis, astroglial proliferation, wound healing, polycystic kidney disease, lung epithelial proliferation or differentiation (e.g. associated with asthmatic airway remodeling or tissue repair), inflammatory arthritis (e.g. rheumatoid arthritis, systemic lupus erythematosus-associated arthritis, psoriatis arthritis) testicular androgen production, thymic epithelial cell proliferation, uterine epithelial cell proliferation, angiogenesis, cell survival, apoptosis, NFκB activation, vascular smooth muscle cell proliferation, restenosis or lung liquid secretion.

[6,7-bis(2-methoxyethoxy)quinazolin-4-yl]-(3-ethynylphenyl)-amine hydrochloride, preferably the stable polymorph B form, is also used for the treatment of a range of leukemias (chronic and acute) and lymphoid malignancies (e.g. lymphocytic lymphomas), diabetes, diabetic and other retinopathies, such as retinophay or prematurity, age-related macular degeneration, solid tumors of childhood, glioma, hemangiomas, melanomas, including intraocular or uveal melanomas, Kaposi's sarcoma, Hodgkin's disease, epidermoid cancers, cancers of the endocrine system (e.g. parathyroid, adrenal glands), bone small intestine, urethra, penis and ureter, atherosclerosis, skin diseases such as eczema and scleroderma, mycoses fungoides, sarcomas of the soft tissues and neoplasm of the central nervous system (e.g. primary CNS lymphoma, spinal axis tumors, brain stem gliomas, or pituitary adenomas).

The treatment of any of the hyperproliferative or additional disorders described above may be applied as a monotherapy, or may involve in addition to [6,7-bis(2-methoxyethoxy)quinazolin-4-yl]-(3-ethynylphenyl)-amine hydrochloride, preferably the stable polymorph B form, application with one or more additional drugs or treatments (e.g. radiotherapy, chemoradiotherapy) that are anti-hyperproliferative, anti-tumor or antihyperplastic in nature. Such conjoint treatment may be achieved by way of simultaneous, sequential, cyclic or separate dosing of the individual components of the treatment. [6,7-bis(2-methoxyethoxy)quinazolin-4-yl]-(3-ethynylphenyl)-amine hydrochloride, preferably the stable polymorph B form, is typically used at doses of 1–7000 mg/day, preferably 5–2500 mg/day, most preferably 5–200 mg/day, for any of the above treatments.

Furthermore, the various forms of N-(3-ethynylphenyl)-6,7-bis(2-methoxyethoxy)-4-quinazolinamine including the mesylate and hydrochloride forms (all polymorph forms) as well as other pharmaceutically acceptable salt forms, and anhydrous and hydrate forms, can be used for treatment, with a therapeutically-effective amount of the aforementioned compounds and a pharmaceutically acceptable carrier, of the specific conditions of NSCLC (non small cell lung cancer), pediatric malignancies, cervical and other tumors caused or promoted by human papilloma virus (HPV), melanoma, Barrett's esophagus (pre-malignant syndrome) and adrenal and skin cancers as well as auto immune and neoplastic cutaneous diseases such as mycoses fungoides, in a mammal, as well as for the chemoprevention of basal or squamous cell carcinomas of the skin, especially in areas exposed to the sun or in persons known to be at high risk for such cancers. In addition, the aforementioned compounds are useful in treatment of atherosclerosis, with epidermal growth factor having been implicated in the hyperproliferation of vascular smooth muscle cells responsible for atherosclerotic plaques (G. E. Peoples et al., Proc. Nat. Acad. Sci. USA 92:6547–6551, 1995).

The compounds of the present invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. The compounds of the present invention are also inhibitors of angiogenesis and/or vasculogenesis.

The compounds of the present invention may also be useful in the treatment of additional disorders in which aberrant expression ligand/receptor interactions or activation or signalling events related to various protein tyrosine kinases are involved. Such disorders may include those of neuronal, glial, astrocytal, hypothalamic, glandular, macrophagal, epithelial, stromal, or blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

In addition to direct treatment of the above ailments with the compounds, the utilization and treatment in these and general applications may be as palliative or neo-adjuvant/adjuvant monotherapy, in blocking epidermal growth factor receptors (EGFR) and for use in treatment of tumors that express a variant form of EGFR known as EGFRvIII as described in the scientific literature (e.g., D K Moscatello et al. Cancer Res. 55:5536–5539, 1995), as well as in a combination with chemotherapy and immunotherapy. As described in more detail below, treatment is also possible with both anti-EGFR and anti-EGF antibody combinations or with combination of inhibitors of MMP (matrix-metalloproteinase), other tyrosine kinases including VEGFR (vascular endothelial growth factor receptor), farnesyl transferase, $CTLA_4$ (cytotoxic T-lymphocyte antigen 4) and erbB2. Further treatments include MAb to VEGFr, and other cancer-related antibodies including rhuMAb-VEGF (Genentech, Phase III), the erbB2 MAb available as Herceptin (Genentech, Phase III), or the avb3 MAb available as Vitaxin (Applied Molecular Evolution/MedImmune, Phase II).

The invention also relates to a pharmaceutical composition and a method of treating any of the mentioned disorders in a mammal which comprises administering to said mammal a therapeutically effective amount of N-(3-ethynylphenyl)-6,7-bis(2-methoxyethoxy)-4-quinazolinamine, preferably in hydrochloride polymorph B form, and a pharmaceutically acceptable carrier.

Combination Therapy

The active compound may be applied as a sole therapy or may involve one or more other materials and treatment agents such as both anti-EGFR and anti-EGF antibody combinations or with combination of inhibitors of MMP (matrix-metallo-proteinase), other tyrosine kinases including VEGFR (vascular endothelial growth factor receptor), farnesyl transferase, $CTLA_4$ (cytotoxic T-lymphocyte antigen 4) and erbB2, as well as MAb to VEGFr, and other cancer-related antibodies including rhuMAb-VEGF, the erbB2 MAb, or avb3.

Thus, the active compound may be applied with one or more other anti-tumor substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide).

In a further embodiment, the compounds of the invention may be administered in conjunction with an anti-angiogenesis agent(s) such as a MMP-2 (matrix-metalloproteinase-2) inhibitor(s), a MMP-9 (matrix-metalloproteinase-9) inhibitor(s), and/or COX-II (cyclooxygenase II) inhibitor(s) in the methods of treatment an compositions described herein. For the combination therapies and pharmaceutical compositions described herein, the effective amounts of the compound of the invention and of the chemotherapeutic or other agent useful for inhibiting abnormal cell growth (e.g., other antiproliferative agent, anti-angiogenic, signal transduction inhibitor or immune-system enhancer) can be determined by those of ordinary skill in the art, based on the effective amounts for the compound described herein and those known or described for the chemotherapeutic or other agent.

The formulations and routes of administration for such therapies and compositions can be based on the information described herein for compositions and therapies comprising the compound of the invention as the sole active agent and on information provided for the chemotherapeutic or other agent in combination therewith.

The invention also relates to production of compounds used in a method for the treatment of a hyperproliferative disorder in a mammal which comprises administering to said mammal a therapeutically effective amount of N-(3-ethynylphenyl)-6,7-bis(2-methoxyethoxy)-4-quinazolinamine hydrochloride in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, bioloical response modifiers, anti-hormones, and anti-androgens.

The compounds are also useful as radiation sensitizers for cancer treatment and may be combined with anti-hormonal therapies. Parameters of adjuvant radiation therapies are for example contained in PCT/US99/10741, as published on 25 Nov. 1999, in International Publication No. WO 99/60023, the disclosure of which is included herein by reference thereto. With such mode of treatment for example, for inhibiting tumor growth, a radiation dosage of 1–100 Gy is utilized preferably in conjunction with at least 50 mg of the pharmaceutical compound, in a preferred dosage regimen of at least five days a week for about two to ten weeks. Thus, this invention further relates to a method for inhibiting abnormal cell growth in a mammal which method comprises administering to the mammal an amount of the compound of the invention, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with the compound of the invention in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

0.3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran -4-carboxylic acid hydroxyamide;

(R) 3-[4-(4-chloro-phenoxy)-benzenesulfonylamino]-tetrahydro-pyran -3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran -4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan -3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

The compound of the present invention can also be used with signal transduction inhibitors, such as other agents that can inhibit EGFR (epidermal growth factor receptor) responses, such as EGFR antibodies, EGF antibodies, and other molecules that are EGFR inhibitors; VEGF (vascular endothelial growth factor) inhibitors, such as VEGF receptors and molecules that can inhibit VEGF; and erbB2 receptor inhibitors, such as other organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and other compounds described in U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as farnesyl protein transferase inhibitors. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

Such conjoint treatment may be achieved by way of the simultaneous, sequential or separate dosing of the individual components of the treatment.

It is expected that the compound of the invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of the compound of the invention, pharmaceutically acceptable salt or solvate thereof, or prodrug thereof, which amount is effective in sensitizing abnormal cells to treatment with radiation. The amount of the compound, salt, solvate, or prodrug in this method can be determined according to the means for ascertaining effective amounts of the compound of the invention described herein.

The subject invention also includes isotopically-labelled compounds, which compounds are identical to the above recited compound of the invention, but for the fact that one or more atoms thereof are replaced by an atom having an atomic mass or mass number different from the atomic mass or mass number usually found in nature. Examples of isotopes that can be incorporated into the compound of the invention include isotopes of hydrogen, carbon, nitrogen and oxygen, such as $^2$H, $^3$H, $^{13}$C, $^{14}$C, $^{15}$N, $^{18}$O and $^{17}$O, respectively. Compounds of the present invention, and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by carrying out the procedures disclosed in the Methods and/or the examples below, and substituting a readily available isotopically labelled reagent for a non-isotopically labelled reagent, using methods well known in the art. Accordingly, reference to the compound of the invention for use in the therapeutic methods and pharmaceutical compositions described herein also encompasses isotropically-labelled forms of the compound.

[6,7-bis(2-methoxyethoxy)quinazolin-4-yl]-(3-ethynylphenyl)-amine hydrochloride, preferably the stable polymorph B form, is typically used at doses of 1–7000 mg/day, preferably 5–2500 mg/day, most preferably 5–200 mg/day, for any of the above treatments.

Patients that can be treated with the compound of the invention, alone or in combination, include, for example, patients that have been diagnosed as having psoriasis, BPH, lung cancer, bone cancer, pancreatic cancer, skin cancer, cancer of the head and neck, cutaneous or intraocular melanoma, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

Activity

The in vitro activity of the compounds of the present invention in inhibiting the receptor tyrosine kinase (and thus subsequent proliferative response, e.g., cancer) may be determined by the following procedure.

The activity of the compounds of the present invention, in vitro, can be determined by the amount of inhibition of the phosphorylation of an exogenous substrate (e.g., $Lys_3$-Gastrin or polyGluTyr (4:1) random copolymer (I. Posner et al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, Methods in Enzymology 146, 82–88 (1987) from A431 cells (American Type Culture Collection, Rockville, Md.) and preincubated in a microfuge tube with EGF (2 µg/ml) in phosphorylation buffer+vanadate (PBV: 50 mM HEPES, pH 7.4; 125 mM NaCl; 24 mM $MgCl_2$; 100 µM sodium orthovanadate), in a total volume of 10 µl, for 20–30 minutes at room temperature. The test compound, dissolved in dimethylsulfoxide (DMSO), is diluted in PBV, and 10 µl is mixed with the EGF receptor/EGF mix, and incubated for 10–30 minutes at 30° C. The phosphorylation reaction is initiated by addition of 20 µl $^{33}$P-ATP/substrate mix (120 µM $Lys_3$-Gastrin (sequence in single letter code for amino acids, KKKGPWLEEEEEAYGWLDF), 50 mM Hepes pH 7.4, 40 µM ATP, 2 µCi γ-[$^{33}$P]-ATP) to the EGFr/EGF mix and incubated for 20 minutes at room temperature. The reaction is stopped by addition of 10 µl stop solution (0.5 M EDTA, pH 8; 2 mM ATP) and 6 µl 2N HCl. The tubes are centrifuged at 14,000 RPM, 4° C., for 10 minutes. 35 µl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., $lys_3$-gastrin) is subtracted from all values as a background and percent inhibition is calculated relative to controls without test compound present. Such assays, carried out with a range of doses of test compounds, allow the determination of an approximate $IC_{50}$ value for the in vitro inhibition of EGFR kinase activity.

Other methods for determining the activity of the compounds of the present invention are described in U.S. Pat. No. 5,747,498, the disclosure of which is incorporated herein.

Pharmaceutical Compositions

The pharmaceutical composition may, for example and most preferably, be in a form suitable for oral administration as a tablet, capsule, pill, powder, sustained release formulations, solution, and suspension. Less preferred (with the mesylate form being the preferred form) are compositons for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Additionally, it is also possible to administer the compound of the invention topically and this may be done by way of creams, jellies, gels, pastes, ointments and the like, in accordance with standard pharmaceutical practice.

The compound of the invention may also be administered to a mammal other than a human. The dosage to be administered to a mammal will depend on the animal species and the disease or disorder being treated. The compound may be administered to animals in the form of a capsule, bolus, tablet or liquid drench. The compound may also be administered to animals by injection or as an implant. Such formulations are prepared in a conventional manner in accordance with standard veterinary practice. As an alternative, the compound may be administered with the animal feedstuff, and for this purpose a concentrated feed additive or premix may be prepared for mixing with the normal animal feed.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

Administration and Dosage

Administration of the compounds of the present invention (hereinafter the "active compound(s)") can be effected by any method that enables delivery of the compounds to the site of action. These methods preferably include oral routes such as in the form of tablets, intraduodenal routes, parenteral injection (including intravenous, subcutaneous, intramuscular, intravascular or infusion), topical, and rectal administration. While parenteral administration is usually preferred, oral administration is preferred for the hydrochloride B polymorph.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

[6,7-bis(2-methoxyethoxy)quinazolin-4-yl]-(3-ethynylphenyl)-amine hydrochloride, preferably the stable polymorph B form, at doses of 1–7000 mg/day, preferably 5–2500 mg/day, most preferably 5–200 mg/day, is also useful for the treatment of patients (as measured, for example, by increased survival times) by using combination therapies, for example in NSCLC (IIIb/V), as a 1$^{st}$ line therapy with carboplatin/paclitaxel or gemcitabine/cisplatin, in NSCLC (IIIb/V), as a 2$^{nd}$ line therapy with taxotere, and in head and neck cancers, as a 2nd line therapy with methotrexate for patients refractory to 5 FU/cisplatin.

[6,7-bis(2-methoxyethoxy)quinazolin-4-yl]-(3-ethynylphenyl)-amine hydrochloride, preferably the stable polymorph B form, at doses of 1–7000 mg/day, preferably 5–2500 mg/day, most preferably 5–200 mg/day, is also useful for the treatment of patients with additional conditions, including pancreatic cancer, with or without gemcitabine co-treatment, as first line therapy, for renal cancer, gastric cancer, prostate cancer, colorectal cancer (e.g. as a 2nd line therapy for patients who have failed 5 FU/LCV/Irinotecan therapy), and also for hepatocellular, bladder, brain, ovarian, breast, and cervical cancers. For such treatments, in advanced disease patients with refractory disease, treatment effectiveness is readily monitored by an increased response rate, an increased time to progression or an increase in survival time.

[6,7-bis(2-methoxyethoxy)quinazolin-4-yl]-(3-ethynylphenyl)-amine hydrochloride, preferably the stable polymorph B form, is typically used at doses of 1–7000 mg/day, preferably 5–2500 mg/day, most preferably 5–200 mg/day, for any of the above treatments.

The examples and preparations provided below further illustrate and exemplify the compounds of the present invention and methods of preparing such compounds. This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

Reaction: Preparation of Compound of Formula 4

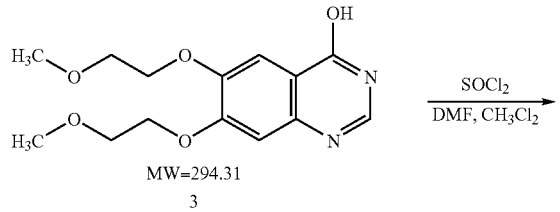

MW=294.31

3

-continued

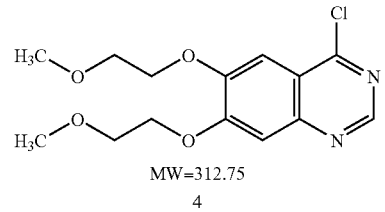

MW=312.75

4

The following materials were used in the synthesis of the compound of formula 4:

| Materials | Quantity | Units | Equivalents/Volumes |
|---|---|---|---|
| Compound of formula 3 | 88.0 | kg | 1 equivalent |
| Thionyl chloride | 89.0 | kg | 2.5 equivalents |
| Dimethylformamide | 11 | kg | 0.5 equivalent |
| methylene chloride | 880.0 | L | 10 L/kg |
| 50% sodium hydroxide solution | as required | L | 1 equivalent |
| Heptane | 880.0 | L | 10 L/kg |

The following procedure is exemplary of the procedure to follow in the synthesis of the formula 4 compound:

88.0 kg of the compound of formula 3, 880.0 L methylene chloride, and 11.0 kg of dimethylformamide were charged to a clean, dry, glass-lined vessel under nitrogen atmosphere. 89 Kg of thionyl chloride were added to the mix while it is maintained at a temperature of a less than 30° C. during the charge. The contents of the reaction vessel were then heated for a minimum of five hours at reflux temperature before sampling for reaction completion and the pH is adjusted to be maintained between 7.0 to 8.0, by using 50% NaOH, as required and the temperature of the reaction mixture is maintained at less than 25° C. The biphasic mixture is stirred for fifteen to twenty minutes and allowed to settle for a minimum of thirty minutes. The layers were separated and the organic layer was concentrated to ⅓ of its volume by removing methylene chloride. 880 L heptane was added with continued distillation of the remaining methylene chloride until the distillate reaches a temperature between 65 and 68° C. The mixture was then cooled to between 10 to 15° C. over 5 hours and granulated for a minimum of 1 hour with the solids being isolated by filtration and washed with 220 L heptane. The solids (formula 4 compound) were dried in a vacuum drier at 45 to 50° C.

Example 2

Alternative Preparation of Compound of Formula 4

In the reaction shown in Example 1, sodium bicarbonate may successfully be used instead of sodium hydroxide as shown in this Example.

| Materials | Quantity | Units | Equivalents/Volumes |
|---|---|---|---|
| Compound of formula 3 | 30.0 | kg | 1 equivalent |
| Thionyl chloride | 36.4 | kg | 3 equivalents |
| Dimethylformamide | 3.75 | kg | 0.5 equivalent |
| methylene chloride | 300 | L | 10 L/kg |

-continued

| Materials | Quantity | Units | Equivalents/ Volumes |
|---|---|---|---|
| 50% sodium hydroxide solution | as required | L | |
| Heptane | 375 | L | 12.5 L/kg |
| Heptane (wash) | 90 | L | 3 L/kg |
| Sodium Bicarbonate | 64.2 | Kg | 7.5 equivalents |

30.0 kg of the compound of formula 3, 300.0L methylene chloride, and 3.75 kg of dimethylformamide were charged to a clean, dry, glass-lined vessel under a nitrogen atmosphere. 36.4 kg of thionyl chloride was added to the mix while it was maintained at a temperature of less than 30° C. during the charge. The contents of the reaction vessel were then heated at reflux temperature for 13 h before sampling for reaction completion. The reaction mixture was cooled to 20–25° C. and added slowly to a stirred solution of sodium bicarbonate 64.2 kg and water 274L cooled to 4° C. so that the temperature was maintained at less than 10° C. The final pH of the mixture was adjusted to within the range 7.0 to 8.0 by using 50% sodium hydroxide solution as required. The biphasic mixture was stirred for fifteen to twenty minutes and allowed to settle for a minimum of thirty minutes at 10–20° C. The layers were separated and the organic layer was concentrated to ⅓ of its volume by removing methylene chloride. 375L of heptane was added with continued distillation of the remaining methylene chloride until the distillate reached a temperature between 65 and 68° C. The mixture was then cooled to 0 to 5° C. over 4 hour and granulated for a minimum of 1 hour with the solids being isolated by filtration and washed with 90L heptane.

The solids (formula 4 compound) were dried in a vacuum drier at 45 to 50° C.

Example 3

Preparation of Compound of Formulas 6 and 2 (Step 2):

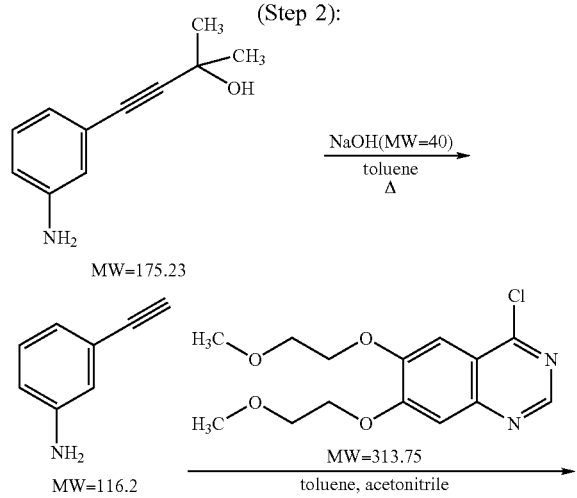

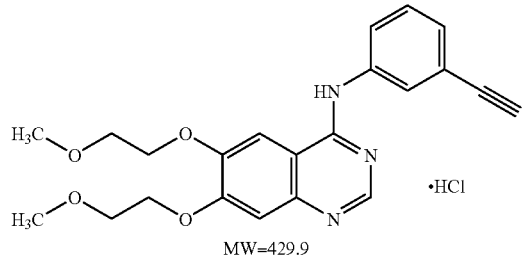

MW=429.9

The following materials were used in the synthesis of the compound of formula 6, as intermediate, and the compound of formula 2:

| Materials | Quantity | Units | Equivalents/ Volumes |
|---|---|---|---|
| Compound of formula 5 | 61.1 | kg | 1.2 equivalents |
| Toluene | 489 | L | 8 L/kg (WRT to formula 5 c'mpd) |
| Sodium hydroxide pellets | 4.5 | kg | 0.16 equivalents |
| Filteraid | 0.5 | kg | 0.017 kg/kg (WRT to c'mpd 5) |
| Compound of formula 4 | 90.8 | kg | 1.0 equivalent |
| Acetonitrile | 732 | L | 12 L/kg (WRT to c'mpd 5) |

Example 4

Preparation of Compound of Formula 2

The following procedure is exemplary of the procedure to follow in the synthesis of the formula 2 compound and intermediate compound of formula 6:

61.1 kg of formula 5 compound, 4.5 kg sodium hydroxide pellets and 489 L-toluene were charged to a clean, dry, reaction vessel under nitrogen atmosphere and the reaction temperature is adjusted to between 105 to 108° C. Acetone was removed over four hours by atmospheric distillation while toluene is added to maintain a minimum volume of 6 L of solvent per kg of formula 5 compound. The reaction mixture was then heated at reflux temperature, returning distillates to pot, until the reaction was complete. The mixture was then cooled to between 20 to 25° C., at which time a slurry of 40.0 L toluene and 0.5 kg filteraid was charged to the reaction mixture and the mixture was agitated for ten to fifteen minutes. The resultant material was filtered to remove filteraid, and the cake is washed with 30 L toluene (compound of formula 6).

The filtrate (compound of formula 6) was placed in a clean, dry reaction vessel under nitrogen atmosphere, and 90.8 kg of the compound of formula 4 was charged into the reaction vessel together with 732 L acetonitrile. The reaction vessel was heated to reflux temperature and well agitated. Agitator speed was lowered when heavy solids appear. When the reaction was complete, the contents of reaction vessel were cooled to between 19 to 25° C. over three to four hours and the contents were agitated for at least one hour at a temperature between 20 and 25° C. The solids (compound of formula 2, polymorph A form, or mixture of polymorph A and B) were then isolated by filtration and the filter cake was washed with two portions of 50 L acetonitrile and dried under vacuum at a temperature between 40 and 45° C.

It has been discovered that the production of the A polymorph is favored by the reduction of the amount of acetonitrile relative to toluene, and particularly favored if isopropanol is used in place of acetonitrile. However, the use of isopropanol or other alcohols as cosolvents is disfavored because of the propensity to form an ether linkage between the alcoholic oxygen and the 4-carbon of the quinazoline, instead of the desired ethynyl phenyl amino moiety.

It has been further discovered that adjusting the pH of the reaction to between pH 1 and pH 7, preferably between pH 2 and pH 5, more preferably between pH 2.5 and pH 4, most preferably pH 3, will improve the rate of the reaction.

Example 5

Recrystallization of Compound of Formula 2 (Which may be in Polymorph A form or a Mixture of Polymorphs A and B) to Polymorph B (Step 3)

Reaction:

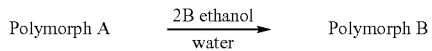

The following materials were used in the conversion of polymorph A (or mixtures of polymorphs A and B) to polymorph B of the compound of formula 2:

| Materials | Quantity | Units | Equivalents/Volumes |
| --- | --- | --- | --- |
| Polymorph A (formula 2) | 117.6 | kg | 1 equivalent |
| 2B-ethanol | 1881.6 | L | 16 L/kg |
| Water | 470.4 | L | 4 L/kg |

The following procedure is exemplary of procedures used to convert polymorph A (or mixtures of polymorphs A and B) into the more thermodynamically stable polymorph B of the compound of formula 2:

117.6 kg of the polymorph A (or mixtures of polymorphs A and B) were charged to a clean, dry, reaction vessel together 1881.6 L 2B-ethanol and 470.4 L water under a nitrogen atmosphere. The temperature was adjusted to reflux (~80° C.) and the mixture was agitated until the solids dissolve. The solution was cooled to between 65 and 70° C. and clarified by filtration. With low speed agitation, the solution was further cooled to between 50 and 60° C. over a minimum time of 2 hours and the precipitate was granulated for 2 hours at this temperature. The mixture was further cooled to between 0 and 5° C. over a minimum time of 4 hours and granulated for a minimum of 2 hours at this temperature. The solids (polymorph B) were isolated by filtration and washed with at least 100 L 2B-ethanol. The solids were determined to be crystalline polymorph B form of [6,7-bis(2-methoxyethoxy)quinazolin-4-yl]-(3-ethynylphenyl)-amine hydrochloride substantially free of the polymorph A from. The solids obtained by this method are substantially homogeneous polymorph B form crystals relative to the polymorph A form. The method allows for production of polymorph B in an amount at least 70% by weight, at least 80% by weight, at least 90% by weight, at least 95% by weight, and at least 98% by weight relative to the weight of the polymorph A. It is to be understood that the methods described herein are only exemplary and are not intended to exclude variations in the above parameters which allow the production of polymorph B in varying granulations and yields, according to the desired storage, handling and manufacturing applications of the compound. The solids were vacuum dried at a temperature below 50° C. and the resultant product was milled to provide the polymorph B in usable form.

Example 6

Clinical Studies Utilizing Treatment with the Stable Polymorph B form of [6,7-bis(2-methoxyethoxy)quinazolin-4-yl]-(3-ethynylphenyl)-amine Hydrochloride The stable polymorph B form of [6,7-bis(2-methoxyethoxy)quinazolin-4-yl]-(3-ethynylphenyl)-amine hydrochloride is a potent, selective and orally active inhibitor of the epidermal growth factor receptor (EFGR) protein-tyrosine kinase, an oncogene that has been associated with the aberrant growth that is characteristic of cancer cells. This compound is being evaluated in clinical trials in normal healthy volunteers and in cancer patients in order to assess its safety profile and effectiveness.

Phase I Clinical Studies

Phase I clinical studies of the stable polymorph B form of [6,7-bis(2-methoxyethoxy)quinazolin-4-yl]-(3-ethynylphenyl)-amine hydrochloride have been effectively completed in volunteers, initially, and subsequently in cancer patients, at single doses ranging from 25–200 mg/day or 100–1600 mg/week. Data from these studies revealed no adverse events that were greater than moderate in severity for a dose of 150 mg/day. In a daily dosing regimen study the dose limiting toxicity at 200 mg/day was diarrhea. This observed side effect was effectively controlled at the 150 mg daily dose level using Loperamide (Imodium®). The second adverse event observed in these studies, and most significant toxicity at 150 mg daily, was a monomorphic acneiform rash analogous to that reported for other EGFR inhibitor agents in clinical trials. This rash had an "above-waist" distribution including face, scalp, neck, arms, chest and back. The rash has a unique histopathology of PMN infiltration with mild epidermal hyperproliferation. It is not consistent with drug hypersensitivity nor does it appear to be a "named" dermatological condition. This rash has not been a significant impediment to patients staying on the Phase II trials. The stable polymorph B form of [6,7-bis(2-methoxyethoxy) quinazolin -4-yl]-(3-ethynylphenyl)-amine hydrochloride has been tested in a total of 290 patients in Phase I and ongoing Phase II studies and demonstrates a well tolerated safety profile. Furthermore, preliminary evidence of effectiveness was observed in Phase I studies. For example, in one Phase I study of 28 patients, 8 patients remain alive over a year after inception of treatment and 12 patients remained alive from 9–22 months.

In order to establish a suitable safety profile, the stable polymorph B form of [6,7-bis(2-methoxyethoxy)quinazolin-4-yl]-(3-ethynylphenyl)-amine hydrochloride is also used at doses of 1–7000 mg/day, preferably 5–2500 mg/day, most preferably 5–200 mg/day, in Phase I clinical combination studies with one or more additional drugs or treatments, preferably selected from one of the following group—Taxol, Gemcitabine, Taxotere, Capcitabine, 5 FU, Cisplatin, Temozolomide, radiation treatment, and chemoradiation treatment.

Phase II and Phase III Clinical Studies

Three Phase II single agent studies of the stable polymorph B form of [6,7-bis(2-methoxyethoxy)quinazolin-4-yl]-(3-ethynylphenyl)-amine hydrochloride in refractory non-small cell lung cancer, advanced head and neck cancer and refractory ovarian cancer, at a 150 mg daily dose were initiated.

Indications of single agent anti-tumor activity for the stable polymorph B form of [6,7-bis(2-methoxyethoxy)quinazolin-4-yl]-(3-ethynylphenyl)-amine hydrochloride was seen in patients with advanced cancers in several different tumor types. For example, initial findings indicate that the stable polymorph B form of [6,7-bis(2-methoxyethoxy)quinazolin-4-yl]-(3-ethynylphenyl)-amine hydrochloride is a well-tolerated oral medication that is active as a monotherapy when administered to patients with advanced head and neck cancer. In preliminary results 3 patients had objective partial responses, while another 9 patients showed evidence of a stabilization of their disease status. The acneiform rash, which is apparently characteristic of all the anti-EGFR inhibitors undergoing clinical testing, was reported in approximately 70% of the first group of patients in this study.

The early data emerging from the 48 patient Phase II study in refractory non-small cell lung cancer (NSCLC) patients also indicates the effectiveness of treatment with the stable polymorph B form of [6,7-bis(2-methoxyethoxy)quinazolin-4-yl]-(3-ethynylphenyl)-amine hydrochloride as a single agent anti-tumor drug for NSCLC. Of the first 19 evaluable patients in the study, 5 had objective partial responses, while another 4 patients showed evidence of a stabilization of their disease status. Partial responses were observed in two patients who had been treated previously with two and three different chemotherapy regimens. Thus it appears that the stable polymorph B form of [6,7-bis(2-methoxyethoxy)quinazolin-4-yl]-(3-ethynylphenyl)-amine hydrochloride is a well tolerated, oral medication which is active in non-small cell lung cancer.

Qualification criteria for the open label, single agent study required the patients to have failed platinum-based chemotherapy and to have tumors that are histopathologically confirmed to be EGFR positive. The primary endpoint in the study is response rate with stable disease and time-to-progression amongst the secondary end-points.

Evidence of anti-tumor activity can also be seen in the patients with ovarian cancer in the on-going Phase II study. In preliminary results 2 patients had objective partial responses, while another 4 patients showed evidence of a stabilization of their disease status. Documented evidence of anti-tumor activity was also seen in other EGFR positive tumor types, including colorectal and renal cell carcinoma, from Phase I studies in cancer patients with multiple tumor types.

What is claimed is:

1. A method of monotherapy for a subject suffering from abnormal cell growth expressing the epidernal growth factor receptor (EGFR) which comprises orally administering to the subject a therapeutically effective amount of a homogenous crystalline polymorph of the hydrochloride salt of N-(3-ethynylphenyl)-6,7-bis (2-methoxyethoxy)-4-quinazolinamine designated the B polymorph that exhibits an X-ray powder diffraction pattern having characteristic peaks expressed in degrees 2-theta at approximately 6.26, 12.48, 13.39, 16.96, 20.20, 21.10, 22.98, 24.46, 25.14, and 26.91 so as to treat the subject, wherein the abnormal cell growth is brain cancer, squamous cell cancer, bladder cancer, gastric cancer, pancreatic cancer, hepatic cancer, glioblastoma multiforme breast cancer, head cancer, neck cancer, esophageal cancer, prostate cancer, colorectal cancer, lung cancer, renal cancer, kidney cancer, ovarian cancer, gynecological cancer, thyroid cancer, non-small cell lung cancer (NSCLC), refractory ovarian cancer, or head and neck cancer.

2. The method of claim 1, wherein the abnormal cell growth is non-small cell lung cancer (NSCLC).

3. The method of claim 1, wherein the abnormal cell growth is refractory ovarian cancer.

4. The method of claim 1, wherein the abnormal cell growth is head and neck cancer.

5. The method of claim 1, wherein the therapeutically effective amount is from about 0.001 to about 100 mg/kg/day.

6. The method of claim 1, wherein the therapeutically effective amount is from about 1 to about 35 mg/kg/day.

7. The method of claim 1, wherein the therapeutically effective amount is from about 1 to about 7000 mg/day.

8. The method of claim 1, wherein the therapeutically effective amount is from about 5 to about 2500 mg/day.

9. The method of claim 1, wherein the therapeutically effective amount is from about 5 to about 200 mg/day.

10. The method of claim 1, wherein the therapeutically effective amount is from about 25 to about 200 mg/day.

11. The method of claim 1, wherein the treatment is a palliative or neo-adjuvant/adjuvant monotherapy.

12. The method of claim 1, wherein the EGFR receptor is the EGFRvIII receptor.

13. The method of claim 1, wherein the therapeutically effective amount is from 100 to 1600 mg/week.

14. The method of claim 1, wherein the therapeutically effective amount is orally administered weekly.

* * * * *